(12) United States Patent
Woodhouse

(10) Patent No.: US 6,612,427 B2
(45) Date of Patent: *Sep. 2, 2003

(54) METHOD AND APPARATUS FOR CONTAINING PROPHYLACTIC ARTICLES

(76) Inventor: Paul Woodhouse, 1181 Main St., Apt D, Rahway, NJ (US) 07065

( * ) Notice: Subject to any disclaimer, the term of this patent is extended or adjusted under 35 U.S.C. 154(b) by 77 days.

This patent is subject to a terminal disclaimer.

(21) Appl. No.: 09/900,191

(22) Filed: Jul. 9, 2001

(65) Prior Publication Data

US 2001/0035358 A1 Nov. 1, 2001

Related U.S. Application Data

(63) Continuation-in-part of application No. 09/481,556, filed on Jan. 11, 2000, now Pat. No. 6,257,400.

(51) Int. Cl.[7] .............................................. B65D 85/14
(52) U.S. Cl. ........................................................ 206/69
(58) Field of Search .................... 206/6.9, 5.1; 128/842, 128/844, 918; 604/347–353

(56) References Cited

U.S. PATENT DOCUMENTS

| | | | | |
|---|---|---|---|---|
| 4,289,232 A | * | 9/1981 | Seibel et al. | 206/37 |
| 5,427,233 A | * | 6/1995 | Zinck et al. | 206/69 |
| 5,657,506 A | * | 8/1997 | Pankow | 15/104.92 |
| 5,740,814 A | * | 4/1998 | Comi | 128/844 |
| 5,862,908 A | * | 1/1999 | Arbin | 206/69 |
| 6,257,400 B1 | * | 7/2001 | Woodhouse | 206/69 |

* cited by examiner

Primary Examiner—David T. Fidei
(74) Attorney, Agent, or Firm—Jerome J. Norris

(57) ABSTRACT

A sanitary and compact container having a recessed compartment for holding condoms and a convex compartment that registers with the recessed compartment. The container is provided with a hinge, an air-tight seal or gasket and a button-snap closure, and is decorative and aesthetically pleasing. The container may be provided with one or more additional compartments for holding additional condoms, spermicide and/or personal lubricant. Condoms may be removed from their wrapper before placement in the container.

10 Claims, 2 Drawing Sheets

METHOD AND APPARATUS FOR CONTAINING PROPHYLACTIC ARTICLES

This is a continuation-in-part to U.S. patent application Ser. No. 09/481,556 filed Jan. 11, 2000 (now U.S. Pat. No. 6,257,400).

BACKGROUND OF THE INVENTION

1. Field of the Invention

The invention pertains in general to sanitary containers, and in particular, to sanitary containers for prophylactics.

2. Discussion of the Related Art

Throughout the years attempts have been made to carry and conceal condoms in a aesthetically, discreet, convenient, easy access, and socially acceptable manner. Such attempts both tried to have the condoms ready for quick access and immediate use while at the same time present the condoms in a visually pleasing and sanitary container.

For instance, U.S. Pat. No. 4,741,434 disclose a keyholder having a case for holding a condom package. Although interesting, this keyholder condom case does not provide easy access as pins must first be removed to use the condom package, followed by opening of the package to access the condom contained therein.

U.S. Pat. No. 4,892,188 disclose a condom case having a container. However, this condom case is not air-tight and therefore not as sanitary or hygienic as needed for proper unpackaged condom usage.

U.S. Pat. No. 5,316,136 disclose a case for housing packaged condoms. The case includes upper and lower lids, and a pair of holes for receiving two separate keys that simultaneously disengage a pair of locking mechanisms within the case. This packaged condom housing arrangement is mechanically intricate, not sufficiently hygenic for unpackaged condom usage, and inconvenient.

Accordingly, the present invention provides a case for carrying condoms that is convenient, sanitary and aesthetically pleasing. Moreover, the present invention case is reusable, lightweight and discreet.

SUMMARY OF THE INVENTION

One object of the present invention to provide a container for prophylactic articles that is discreet and hygienic.

Another object of the invention is to provide a container for prophylactic articles that is reusable and aesthetically pleasing.

A further object of the invention is to provide a container for prophylactic articles that can be efficiently manufactured at a low cost.

A yet further object of the invention is to provide a method for containing unpackaged prophylactic articles in a sanitary manner.

A further object yet still of the invention is to provide a method for containing a prophylactic article that is convenient and easy to use.

BRIEF DESCRIPTION OF THE DRAWINGS

The foregoing and other objects, aspects and advantages of the present invention will be better understood from the following detailed description of preferred embodiments of the invention with reference to the drawings, in which.

DETAILED DESCRIPTION OF THE PREFERRED EMBODIMENT

Figure 1:
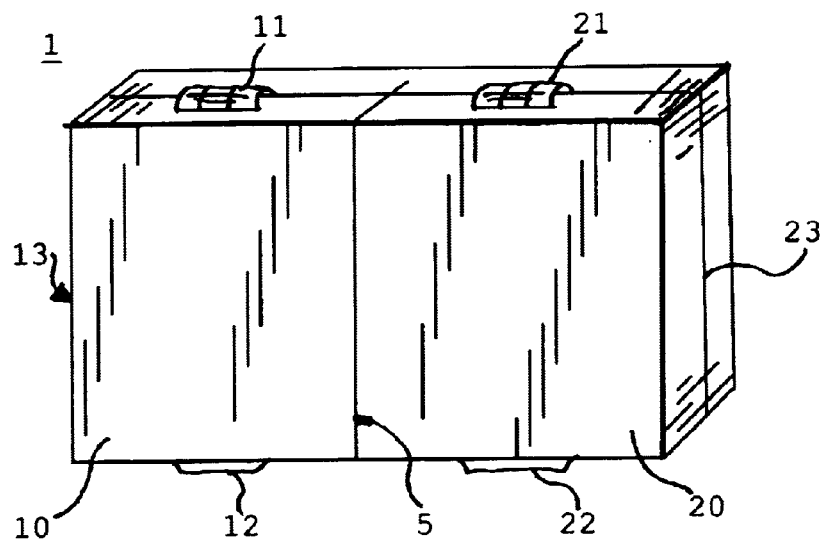
FIG. 1 shows an overall view of the prophylactic case of the present invention.

FIG. 1 shows the prophylactic container or condom storage case of the present invention, which is generally designated by reference numeral 1. Another term for the prophylactic article container of the present invention is simply a condom case.

Figure 2:
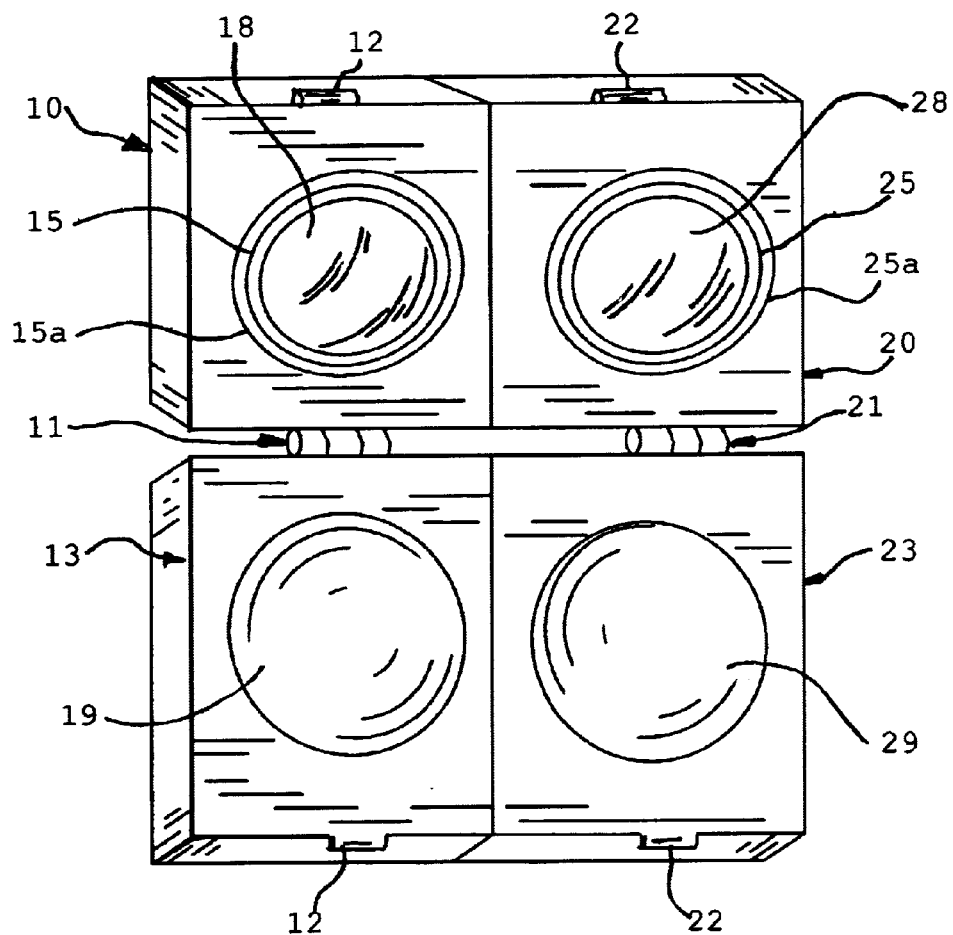
FIG. 2 shows an internal view of the prophylactic case of the present invention.
Figure 3:
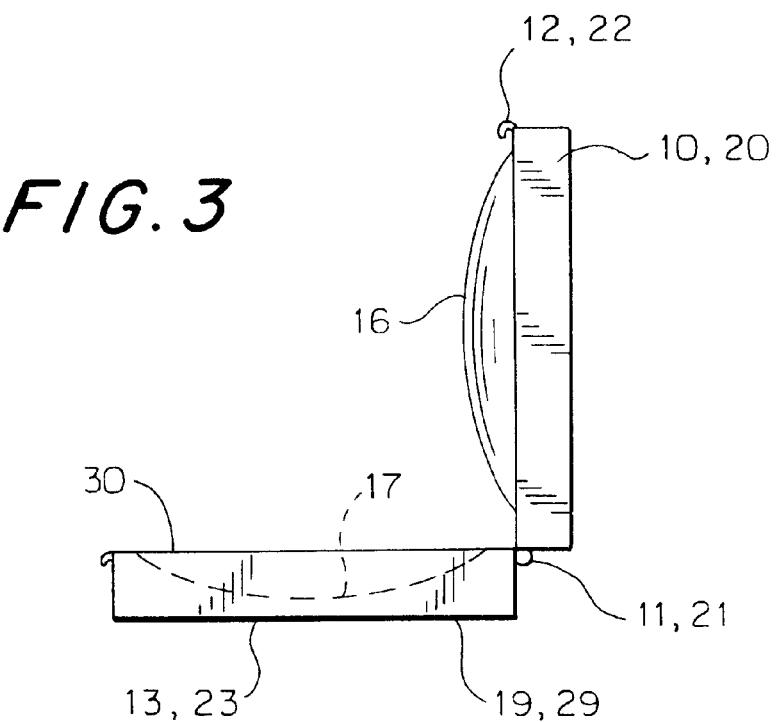
FIG. 3 shows a side view of the prophylactic case in the open position.
Figure 4:
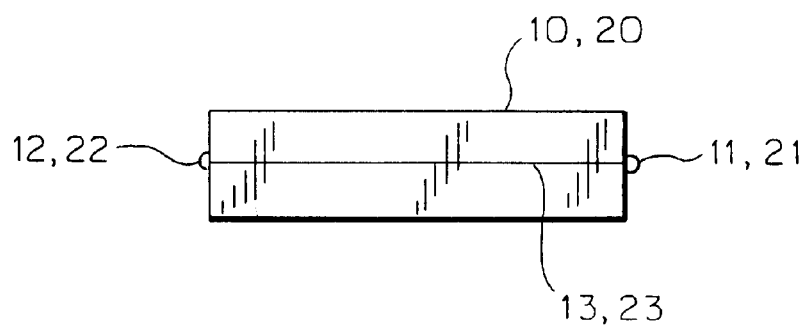
FIG. 4 shows a side view of the prophylactic case in the closed position.

The condom case 1 may take on almost any visually pleasing appearance or form, but is shown in FIG. 1 and in the remaining FIGS. 2–4, as having an overall rectangular shape.

The condom case 1 of the present invention can be formed of any material, including molded plastic, carved wood, stainless steel, copper, glass, carved stone, extruded aluminum, etc.

What is meant by the term prophylactic article with respect to the present invention is a condom, especially the male-use condom, which is also known simply as a male condom. However, the term prophylactic article can also refer to a female-use condom, which is also known simply as a female condom. Thus, the present invention can be suitably used to contain a female condom as well as a male condom. Throughout the entire discussion presented herein, the term condom is meant to refer to either a male condom or a female condom. Furthermore, it is contemplated that, in the sense that a diaphragm is also a type of prophylactic article, the present invention prophylactic case can be used to contain a diaphragm.

The size of the condom case 1 is selected based upon whether it is to contain a male condom or a female condom, which may tend to be larger in size than the male condom. The size of the condom case 1 can also be selected based upon the size of the condom it is to contain. For instance, a larger case 1 should be chosen to contain a larger size condom, or a smaller size condom case 1 should be chosen to contain a smaller size condom.

The condom case 1 shown in FIG. 1 is configured to hold two condoms in that the condom case 1 is provided with two compartments, such that each compartment is intended to hold one condom. However, the condom case 1 of the present invention can be designed to hold any number of condoms, from one to several, provided that each condom is situated in its own compartment.

The condom case 1 shown in FIG. 1 is provided with two compartments delineated by a break 5 which indicates the separation between the two compartments. The two compartments are identical in size, shape and configuration. Thus, unless otherwise indicated, any discussion of the structure and arrangement of one compartment similarly applies to the other compartment. However, for ease of discussion one compartment will be denoted as a first compartment and the other compartment will be denoted as a second compartment.

The first compartment is provided with a lid 10, a hinge 11, a clasp 12, and a base 13 which mates with the lid 10. Similarly, the second compartment is provided with a lid 20, a hinge 21, a clasp 22 and a base 23 which mates with the lid 20. The lids 10, 20, the hinges 11, 21, the clasps 12, 22, and the bases 13, 23 of the first compartment and the second compartment respectively, are identical in size, shape and construction. It is necessary for the lid 10 to be matched in size and construction to the base 13 and the lid 20 to be matched in size and construction to the base 23 in order that the first compartment and the second compartment will close and seal properly in an air tight manner, thereby making the condom case 1 of the present invention hygienic and sanitary when the condom is placed unpackaged into the container.

The lid 10 is connected to the base 13 by a hinge 11. Similarly, the lid 20 is connected to the base 23 by a hinge 21. Each hinge 13, 23 allows the lids 10, 20, respectively to pivot smoothly from a closed position to an open position. Any type of hinge is suitable, so long as the hinge chosen provides both secure and dependable attachment of each lid 10, 20 to its respective base 13, 23, and smooth and convenient opening and closing movement.

FIG. 1 shows the lids 10, 20 in their closed positions thereby showing only the external features of the condom case 1 of the present invention.

The lid 10 is releasably secured to the base 13 by a clasp 12. Similarly, the lid 20 is releasably secured to the base 23 by a clasp 22. Each clasp 12, 22 allows the lids 10, 20 to be conveniently opened when access to the condom contained in each compartment is desired. Any type of clasp is suitable, so long as the clasp chosen provides both secure and dependable connection of each lid to its respective base, and quick and convenient opening when access to the condom contained in the compartment is desired and effortless closing when access to the compartment is no longer needed.

Although the condom case 1 shown in FIG. 1 shows the first compartment and the second compartment in side-by-side disposition in right-to-left arrangement, the condom case 1 of the present invention can be configured with the first compartment and the second compartment being in top-to-bottom arrangement, or even a back-to-back arrangement. Nevertheless, it is essential that each compartment is provided with a lid, such as lids 10, 20, which mates with a base, such as bases 13, 23, a hinge which allow the lid to open and close, such as hinges 11, 21 and a clasp which secures the lid to the base, such as clasps 12, 22.

FIG. 2 shows the condom case 1 of the present invention with the first and second compartments in their open positions so as to expose the internal features of each compartment. The internal construction and layout of the first compartment is identical to that of the second compartment, thus, unless otherwise indicated, any discussion of the structure and arrangement of one compartment similarly applies to the other compartment.

The most significant internal feature of the first compartment is its capacity to form an air-tight seal 15, due to a convex formation or structure in the lid 10 and a recess or concave formation in the base 13. Similarly, the most significant internal feature of the second compartment is an air-tight seal 25, due to a convex formation or structure in the lid 20 and a recess or concave formation in the base 23. The air-tight seal 15 is due to registry of the convex and concave formations when the lid 10 of the first compartment is in the closed position. Likewise, the air-tight seal 25 is due to registry of the convex and concave formation corresponding surfaces or when the lid 20 of the second compartment is in the closed position. The air-tight seal may be augmented by a gasket seal 15*a* an 25*a* surrounding its periphery, and the gasket seal may be any suitable plastic, elastomer or rubber.

The air-tight seals 15, 25 make the first and second compartments suitable for storing the unpackaged prophylactic in a hygienic and sanitary manner, thereby making the prophylactic safe for use when the lid of either compartment is opened. In other words, when the condom is removed from its wrapper, placed in the second compartment and air-tight sealed by closing the first compartment over the second compartment until ready for use, the condom will not be contaminated, deteriorate or experience any dehydration, and will therefore be reliably ready for use.

FIG. 3 shows a side view of the condom case of the present invention. The condom case 1 shown in FIG. 3 is in the open position, that is its lid is in the extended position relative to its base. Since the internal construction and layout of the first compartment is identical to that of the second compartment, any discussion of the structure and arrangement of one compartment similarly applies to the other compartment so that the depiction in of FIG. 3 is to be construed as representing either the first compartment or the second compartment.

The convex formation 16 in the lid 10, 20 fits in registry with the concave formation 17 to form the air-tight seal. A typical condom for use with the condom case 1 of the present invention is represented by reference numeral 30. The condom is seated in the recess or concave formation of the base 19, 29. All remaining components and features of the condom case of the present invention are the same as discussed with respect to FIG. 1 and FIG. 2.

Due to the fact that a condom can be removed from its wrapper in advance before placement in the condom case 1, the present invention prevents unpleasant and distracting preparation (such as wrapper noise and fumbling in darkness) of a condom immediately before use. By using the condom case of the present invention, spontaneous and pleasant condom use is assured.

FIG. 4 shows a side view of the condom case 1 of the present invention with the lid 10, 20 in the closed position, such that the clasps 12, 22 are fully engaged and the air-tight seals 15, 25 in place. The condom 30 is securely and properly contained within the case 1 in a sanitary manner. Thus, when either lid 10, 20 is opened, the condom 30 is conveniently exposed and will be ready for use.

Although not shown in drawing FIGS. 1–4, the condom case 1 of the present invention can easily be provided with a separate compartment to receive therein a tube of personal lubricant which may be used as additional lubricant or additional spermicide as necessary. The condom case of the present invention may also be provided with a compartment adapted to receive therein moist towelettes or other clean-up materials, which would assist in hygienic disposal of a used condom as well as aiding in pleasant and tasteful clean-up.

The additional compartments can be made into either or both the lid 10, 20 or the base 13, 23 of the condom case 1 without distracting from the overall structure and function of the case 1 already discussed.

While the invention has been particularly shown and described with reference to a preferred embodiment hereof, it will be understood by those skilled in the art that several changes in form and detail may be made without departing from the spirit and scope of the invention.

I claim:

1. A receptacle for maintaining an article in a sanitary condition, said receptacle comprising: first and second congruent convex and concave section means that form an air-tight sealed compartment when closed, the first and second section means being hingedly connected together, said first section means having a convex configuration formed in its perimeter and a gasket seal around its perimeter and said second section means having a concave or recess configuration formed in its perimeter, the convex configuration of one section being configured to mate with the recess configuration of the other section means to form an air-tight seal, said recess section further including a region for containing an unpackaged condom, whereby said receptacle maintains said unpackaged condom in a sanitary condition when the first and second congruent section means are mated together or in registry.

2. The receptacle of claim 1, wherein the first and second sections are circular.

3. The receptacle of claim 1, further comprising an area to receive therein a separable container.

4. A method for sanitarily preserving in a container for later use an unpackaged prophylactic article, the container having hingedly joined first and second congruent convex and concave section means which form an air-tight seal when joined, said first section means having a convex configuration formed in its perimeter and a gasket seal around its perimeter, said second section means having space to accommodate said unpackaged prophylactic article in a sanitary manner, the method comprising:

removing the prophylactic article from a sealed envelope;

placing the prophylactic article within said space of said second section concave means; and joining the first and second convex and concave section means together to form an enclosed air-tight sealed prophylactic article within the container.

5. The method of claim 4, wherein said prophylactic article is a condom.

6. A method for sanitarily preserving in a container for later use an unpackaged prophylactic article, the container having hingedly joined first and second congruent convex and concave section means which form an airtight seal when joined, and a compartment means for receiving a separable vessel therein, said first section means having a convex configuration formed in its perimeter and a gasket seal around its perimeter, said second means having space to accommodate the unpackaged prophylactic article in a sanitary manner, the method comprising:

removing the article from a sealed envelope; placing the article within the space of said second concave section means; and joining the first and second convex and concave sections together to form an enclosed prophylactic article within the container.

7. The method of claim 6, wherein said prophylactic article is a condom.

8. The receptacle of claim 2 wherein said gasket seal is selected from the group consisting of plastic, an elastomer or rubber.

9. The method of claim 5 wherein said gasket seal is selected from the group consisting of plastic, an elastomer or rubber.

10. The method of claim 7, wherein said gasket seal is selected from the group consisting of plastic, an elastomer or rubber.

* * * * *